United States Patent
Kolter et al.

(10) Patent No.: US 10,912,835 B2
(45) Date of Patent: Feb. 9, 2021

(54) PRODUCTION OF PHARMACEUTICAL PROTECTIVE COATINGS WITH GOOD RESISTANCE IN A NEUTRAL ENVIRONMENT

(71) Applicant: BASF SE, Ludwigshafen (DE)

(72) Inventors: Karl Kolter, Limburgerhof (DE); Silke Gebert, Grünstadt (DE); Michael Klemens Müller, Haßloch (DE); Maximilian Angel, Schifferstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/848,124

(22) Filed: Dec. 20, 2017

(65) Prior Publication Data
US 2018/0110858 A1 Apr. 26, 2018

Related U.S. Application Data

(62) Division of application No. 13/790,101, filed on Mar. 8, 2013, now abandoned.

(60) Provisional application No. 61/608,655, filed on Mar. 9, 2012.

(51) Int. Cl.
| | | |
|---|---|---|
| *A61K 47/32* | (2006.01) | |
| *A61K 9/00* | (2006.01) | |
| *A61K 47/12* | (2006.01) | |
| *A61K 9/28* | (2006.01) | |
| *A61K 9/50* | (2006.01) | |

(52) U.S. Cl.
CPC ............ *A61K 47/32* (2013.01); *A61K 9/0002* (2013.01); *A61K 9/282* (2013.01); *A61K 9/2846* (2013.01); *A61K 9/5015* (2013.01); *A61K 9/5026* (2013.01); *A61K 47/12* (2013.01)

(58) Field of Classification Search
None
See application file for complete search history.

(56) References Cited

U.S. PATENT DOCUMENTS

| | | |
|---|---|---|
| 4,433,076 A | 2/1984 | Bauer et al. |
| 7,175,857 B2 | 2/2007 | Petereit et al. |
| 2009/0220553 A1 | 9/2009 | Saeed |
| 2011/0033532 A1 | 2/2011 | Angel et al. |
| 2012/0059054 A1 | 3/2012 | Angel et al. |
| 2012/0076858 A1 | 3/2012 | Kolter et al. |

FOREIGN PATENT DOCUMENTS

| | | |
|---|---|---|
| DE | 1219175 B | 6/1966 |
| DE | 2135073 A1 | 2/1973 |
| DE | 2512238 B1 | 5/1976 |
| DE | 10239999 A1 | 3/2004 |
| EP | 0088951 A2 | 9/1983 |
| EP | 0262326 A2 | 4/1988 |
| GB | 1097054 A | 12/1967 |
| WO | 97/42255 A1 | 11/1997 |
| WO | 00/05307 A1 | 2/2000 |
| WO | 02/067906 A1 | 9/2002 |
| WO | 2004/019918 A1 | 3/2004 |
| WO | 2007/017452 A2 | 2/2007 |
| WO | 2007/051743 A2 | 5/2007 |
| WO | 2007/065845 A1 | 6/2007 |
| WO | 2007/065846 A2 | 6/2007 |
| WO | 2009/016258 A1 | 2/2009 |
| WO | 2010/139654 A2 | 12/2010 |
| WO | 2012/031934 A1 | 3/2012 |
| WO | 2012/041788 A1 | 4/2012 |
| WO | 2012/089778 A1 | 7/2012 |
| WO | 2012/116940 A1 | 9/2012 |
| WO | 2012/116941 A1 | 9/2012 |
| WO | 2013/045352 A1 | 4/2013 |
| WO | 2013/131986 A1 | 9/2013 |

OTHER PUBLICATIONS

European Search Report in EP12158728, dated Jun. 6, 2012, 2 pages.
Kollicoat Smartseal 30D, BASF, Oct. 2010.
PCT Search Report in PCT/EP2013/054549, dated Sep. 4, 2013, 3 pages.

*Primary Examiner* — Isis A Ghali
(74) *Attorney, Agent, or Firm* — Servilla Whitney LLC

(57) ABSTRACT

Pharmaceutical coatings obtained from coating compositions based on film-forming copolymers of N,N-diethylaminoethyl methacrylate (DEAEMA) and methyl methacrylate (MMA) comprising a weight ratio of DEAEMA:MMA in the range of 35:65 to 55:45, where the copolymers are present partially neutralized with $C_3$-$C_{10}$-dicarboxylic acids.

16 Claims, No Drawings

PRODUCTION OF PHARMACEUTICAL PROTECTIVE COATINGS WITH GOOD RESISTANCE IN A NEUTRAL ENVIRONMENT

CROSS-REFERENCE TO RELATED APPLICATIONS

This application is a divisional of copending U.S. application Ser. No. 13/790,101, filed Mar. 8, 2013, which claims the benefit under 35 U.S.C. § 119(e) to U.S. Provisional Application No. 61/608,655, filed Mar. 9, 2012, the entire content of which are incorporated herein by reference in their entireties

FIELD

The present invention relates to pharmaceutical protective coatings with good resistance in a neutral environment, where, for the purpose of odor masking or for protecting against moisture, pharmaceutical dosage forms are provided with a film coating based on a cationic copolymer present in partially neutralized form which is obtained by means of free-radical emulsion polymerization of a monomer mixture comprising N,N-diethylaminoethyl methacrylate. The present invention also relates to the production of corresponding coatings and use of corresponding coating compositions for producing protective coatings with good resistance in a neutral environment.

BACKGROUND

When producing pharmaceutical dosage forms of unpleasant tasting active ingredients, there is the fundamental problem of providing the dosage forms with coatings which, on the one hand, permit good taste masking in the neutral environment of the oral cavity, but on the other hand do not have excessively large layer thicknesses. This problem also arises in the production of coated drug forms which are provided with protective coatings for the purpose of protecting moisture-sensitive active ingredients.

Excessively thick coatings are not only esthetically unsatisfactory, because they are more rough than beautifully smooth, but also economically unsatisfactory because more coating composition is required to produce greater layer thicknesses and, moreover, the processing times are longer. Added to this is the fact that excessively thick coatings cause an undesired slower release of the active ingredient in the acidic environment of the stomach, where they are supposed to release the active ingredient as quickly as possible. The aim when developing coating compositions will therefore always be to produce the thinnest possible film coatings, although these have to satisfy the functional demands, as in the present case of taste masking. Desirable application amounts are therefore usually in the range from 1 to 20 mg/cm$^2$.

The coatings also have to be stable for an adequate time in respect of the taste masking. Especially in the case of dosage forms which disintegrate rapidly in the mouth (so-called "Oral Dispersible Tablets"), in which active ingredient crystals or active ingredient micropellets provided with a taste-masked coating are embedded into a matrix which disintegrates rapidly in the oral environment, it often arises that the coated active ingredient crystals or micropellets get caught up in interdental spaces for a while. If the coating then has inadequate denseness to disintegration in the neutral environment of the oral cavity, then unpleasant taste sensations can occur as a result. The requirement placed on suitable coatings is therefore adequate resistance to release of the active ingredient at neutral pH values of at least one hour, preferably even of two hours.

A further requirement is the good redispersibility in water of the film-forming polymers which form the basis of the coating compositions used. The film-forming polymers used for the taste masking are usually pH-dependent soluble polymers which are water-insoluble in a neutral environment, but in most cases dissolve rapidly in the acidic environment of the stomach in order to facilitate a rapid release of the active ingredient.

For the provision of binders for drug coatings with a low residual monomer content, DE-B 2512238 teaches the use of a powder obtained by spray-drying a polymer dispersion for producing coating solutions for these drug forms. As regards the dispersions used for the spray-drying, reference is made to DE 1090381, DE 1219175 and DE 2135073. DE 3049179 A1 is an application of addition to DE 2512238 and relates to the use of a powder obtained by spray-drying according to the teaching of the last-mentioned document in the form of an aqueous suspension which additionally comprises a plasticizer for producing coatings by thermogelation.

WO 00/05307 deals with the provision of coatings and binders for drug forms which comprise (meth)acrylate copolymers which have monomer radicals with tertiary amino groups, the intention being for simple dry or aqueous further processing to be possible.

WO 02/067906 relates to coating and binding compositions having improved water-vapor permeability compared with those described in WO 00/05307. Here, the coating and binding compositions are produced using a mixture which comprises (a) a copolymer of $C_1$-$C_4$-esters of (meth)acrylic acid and further (meth)acrylate monomers with functional tertiary ammonium groups in powder form having an average particle size from 1 to 40 µm, (b) an emulsifier with an HLB value of at least 14 and (c) a $C_{12}$-$C_{18}$-monocarboxylic acid or a $C_{12}$-$C_{18}$-hydroxyl compound.

WO 2004/019918 describes coating and binding compositions which correspond to those described in WO 00/05307 and WO 02/067906 as regards their composition.

EP88951 A2 describes a process for coating drugs using a water-dispersed coating composition based on emulsion polymers, where the coating compositions may be partially present in salt form. The coating compositions can also be obtained from redispersed powders.

WO 97/42255 describes the spray-drying of polymer powders that can be redispersed in aqueous solution and comprise free acid- or base-carrying copolymers, where, before the spray drying, the pH values of the dispersions have to be adjusted with the help of a buffer system.

EP 262326 A2 describes a process for producing a redispersible plastics powder.

WO 2009/016258 discloses the production of the aqueous polymer dispersions of cationic polymers based on N,N-diethylaminoethyl methacrylate as are used according to the invention and the use thereof for the coating of drugs. Although it is described that the cationic polymers can be partially neutralized a series of inorganic and organic acids is listed quite generally as being suitable for the partial neutralization.

With the coating compositions known hitherto which are present in partially neutralized form, however, there is the problem that the dosage forms coated therewith have an unsatisfactory resistance to premature disintegration in the neutral environment of the oral cavity. The redispersibility is often also unsatisfactory.

SUMMARY

Embodiments of the present invention to provide coating compositions which impart good resistance to premature active ingredient release to a pharmaceutical dosage form, and at the same time also have a good redispersibility in water.

Accordingly, pharmaceutical film-forming coatings obtained from coating compositions based on copolymers of N,N-diethylaminoethyl methacrylate and methyl methacrylate in the weight ratio of the monomers of 35:65 to 55:45, where the copolymers are present partially neutralized with $C_3$-$C_{10}$-dicarboxylic acids, have been found.

DETAILED DESCRIPTION

According to one preferred embodiment, the coating compositions are applied in application amounts of 1 to 20 mg/cm$^2$, and in the case of an application amount of 4 mg/cm$^2$, the coatings have a resistance to release of the active ingredient in the aqueous environment at pH 6.8 of at least 80% after 30 min.

Furthermore, a method for producing coating compositions for coatings of dosage forms comprising at least one pharmaceutical active ingredient with a resistance to premature release of the active ingredient has been found, where the coating compositions comprise, as film-forming polymers, copolymers of N,N-diethylaminoethyl methacrylate and methyl methacrylate in the weight ratio of the monomers of 35:65 to 55:45, wherein the copolymers in the coating composition are partially neutralized with $C_3$-$C_{10}$-dicarboxylic acids.

According to a preferred embodiment, the coating compositions are obtained in powder form and redispersed in water prior to application to the dosage form.

Furthermore, the use of film-forming coating compositions for pharmaceutical dosage forms based on copolymers of N,N-diethylaminoethyl methacrylate and methyl methacrylate in the weight ratio of the monomers of 35:65 to 55:45, where the copolymers are present partially neutralized with $C_3$-$C_{10}$-dicarboxylic acids, for protecting active ingredient-containing pharmaceutical dosage forms against premature active ingredient release in an aqueous environment at pH 6.8 has been found.

The resistance to premature release of the pharmaceutical active ingredient in an aqueous environment at pH values in the region of 6.8 is determined with the help of the so-called "paddle model". This measurement method is described in the USP. For this, the coated dosage forms are tested in phosphate buffer at pH 6.8+/−0.05 with the help of a so-called "paddle apparatus" (apparatus 2) according to USP. The phosphate buffer is prepared by dissolving 34.025 g of potassium dihydrogen phosphate in water in a calibrated 5 l measuring flask, adding 112 ml of 1 molar NaOH and topping up to the calibration mark of the 5 l measuring flask.

Coatings according to the invention satisfy the criterion that, for an application amount of 4 mg/cm$^2$, they have a resistance to release of the active ingredient in an aqueous environment at pH 6.8 of at least 80% after 30 min.

Measurement takes place under atmospheric pressure at 25° C. The release of the active ingredient takes place by photometric determination. The release is determined at intervals of 30 min.

According to the invention, a resistance of 80% after 30 min means that, after 30 min, not more than 20% of the active ingredient has been released. Preferably, the resistance after 30 min is 100%, which means that, within this period, no detectable amounts (less than 2%) of active ingredient are released from the dosage forms. After 60 min, the resistance at pH 6.8 should be at least 60%.

Dicarboxylic acids suitable according to the invention have a chain length of from 3 to 10 carbon atoms. Suitable dicarboxylic acids are, in particular, unbranched dicarboxylic acids which have terminal acid groups. Suitable dicarboxylic acids are also those which are substituted with one or two hydroxy groups.

According to the invention, for the purposes of the partial neutralization, preference is given to using dicarboxylic acids which have a first $pK_a$ value of greater than 2 and a second $pK_a$ value of greater than 4. Particular preference is given to using dicarboxylic acids which have a first $pK_a$ value of greater than 2.5 and a second $pK_a$ value of greater than 5. The $pK_a$ value is the negative base ten logarithm of the acid constant, where the acid constant at 25° C. and atmospheric pressure is intended.

Suitable dicarboxylic acids which carry no further substituents besides the acid groups are the saturated alkanedicarboxylic acids malonic acid, succinic acid, glutaric acid, adipic acid or sebacic acid. Suitable alkanedicarboxylic acids substituted with one or two hydroxy groups are malic acid (2-hydroxysuccinic acid) or tartaric acid (2,3-dihydroxysuccinic acid). A suitable unsaturated dicarboxylic acid is primarily fumaric acid.

It is also possible to use mixtures of such dicarboxylic acids. Thus, it may be recommended to mix dicarboxylic acids which produce a particularly good resistance of the coatings with those acids which produce a particularly good redispersibility of the powders. Suitable mixtures are e.g. adipic acid with sulfuric acid or succinic acid with oxalic acid.

Partial neutralization within the context of the invention means that 2 to 15, preferably 4 to 10 mol % of the diethylaminoethyl groups are present in salt form.

With respect to the preparation of the copolymers of methyl methacrylate and N,N-diethylaminoethyl methacrylate serving as film formers in the coatings by emulsion polymerization, reference is made expressly to the disclosure in WO 2009/016258.

The copolymers present in the dispersions preferably have a K value (determined in accordance with Fikentscher on a 1% strength solution in N-methylpyrrolidone (NMP)) in the range from 40 to 60.

The glass transition temperature $T_G$ determined by means of DSC "Differential Scanning Calorimetry" is preferably in a range from 40 to 70° C., particularly preferably 52 to 62° C. Here, the samples are firstly heated to 150° C. and then rapidly cooled from 150° C. The measurement of the glass transition temperature takes place at a heating rate of 20° K/min. The minimum film-forming temperature is determined in accordance with the method described in DIN ISO 2115 and is in the range from 40 to 70° C., preferably 50 to 65° C. The measurement accuracy of the method is in the region of plus/minus 5° C.

The copolymers present in the dispersions are essentially random copolymers.

The average particle diameter of the polymer particles present in the polymer dispersion (determined by means of analytical ultracentrifuge) is preferably in a range from 70 to 200 nm, particularly preferably from 80 to 150 nm, in particular from 90 to 130 nm. The particle size distribution is preferably essentially unimodal.

The LT value of the aqueous dispersions used according to the invention, determined on a 0.01% strength dispersion in water (2.5 cm cuvette, white light), is preferably at least 70%, particularly preferably at least 80%. The determination of the light transmission is described e.g. in Dieter Distler, Wässrige Polymerdispersionen [Aqueous polymer dispersions], Wiley-VCH (1999), p. 40.

Particular preference is given to a copolymer which has a weight ratio of methyl methacrylate (MMA) to diethylaminoethyl methacrylate (DEAEMA) of 55:45. Such a copolymer is also commercially available as Kollicoat® Smartseal, BASF SE.

According to the invention, the C3-C10-dicarboxylic acids specified at the start are added to the copolymer power or to the corresponding aqueous dispersion. Preferably, amounts of acid are added such that the basic groups are present partially in the form of the acid salts. Thus, 1 to 20 mol % of the basic groups can be present in salt form, preferably 2 to 15 mol %, particularly preferably 5 to 10 mol % of the basic groups are neutralized.

The partial neutralization of the copolymer of MMA/DEAMA can take place either in the aqueous primary dispersion, or else on the powder or during or after aqueous redispersion of a powder. The copolymer in powder form can be obtained by spraying processes or by freeze-drying.

Thus, for example, the dicarboxylic acids can be added to the aqueous polymer dispersion prior to a spray-drying. If the acid is incorporated prior to the spray drying, then this can be stirred into the aqueous dispersion using customary methods. According to a further embodiment, a partially neutralized aqueous primary dispersion can be converted to the powder form by freeze-drying.

According to another embodiment, the acid can also be added before or during the redispersion of a powder produced beforehand from the primary dispersion. In the case of addition to a powder, the incorporation of the acid into the polymer powder can take place such that firstly the polymer powder is coarsely predispersed by means of a simple stirrer, then the acid is added and complete redispersion is achieved by means of further stirring. The redispersion is usually very rapid and, after just 10 min, finely divided dispersates are present. In a modified procedure, it is also possible to firstly introduced the acid in water as initial charge and to add the polymer powder to this with stirring. According to a further embodiment of the invention, the polymer powder and the acid are firstly mixed and this powder mixture is introduced into water. According to this embodiment, a completely neutralized polymer powder can also firstly be prepared, which is then adjusted to the desired degree of partial neutralization by mixing with an unneutralized polymer powder.

The amounts by weight of acids to be used in individual cases is governed by the particular molecular weight of the C3-C10-dicarboxylic acid and the desired degree of neutralization.

Preferably, the treatment with acids is carried out such that the pH of the aqueous dispersion, of the powder or of the powder redispersed in water is in the range from 5 to 9. Particularly preferably, the addition of the acid or of the acidic salt is added such that the pH of the aqueous dispersion, of the powder or of the water-redispersed powder is in the range from 6 to 8.

As already mentioned, embodiments of the invention relate to the partial neutralization of the copolymers of MMA/DEAMA in powder form. Preferred procedures for producing the powder form of the copolymers are spraying processes.

The solids content of the dispersions used according to the invention for the spraying processes is preferably 10 to 50% by weight, particularly preferably 20 to 40% by weight. In the case of a prior purification of the dispersion by means of ultrafiltration, the dispersions used according to the invention preferably have solids contents which are within these ranges before and after the ultrafiltration. It is of course likewise possible to subject a diluted polymer dispersion to a concentration by ultrafiltration prior to the spraying process.

Preferably, the coating compositions used for producing the coatings according to the invention are obtained by redispersion in water, the powder obtained by a spraying process being redispersed using low-shear stirring apparatuses at revolutions up to 1000 rpm. Surprisingly, it is also possible to use high-shear dispersing apparatuses at revolutions of >5000 rpm. This can take place according to the invention without the fine particles formed during the redispersion agglomerating and the preparation coagulating.

The average particle size of the polymer powder redispersed in water is at most 5 times, preferably at most 3 times, particularly preferably at most 2 times, that of the underlying primary dispersion.

Average particle sizes refer here to the Z-Average value, which is determined by light scattering by means of a "Malvern Zetasizer nano S" as Z-Average value.

Coating compositions can be prepared e.g. by intimately mixing a by redispersing the polymer powder obtained according to the invention to give an aqueous polymer dispersion, to which preferably at least one further auxiliary is added.

Conversion of the aqueous polymer dispersions to the powder form can take place by means of spraying processes. Suitable spraying processes are in principle spray-drying, agglomerating spray-drying, spray granulation (spray fluidized-bed drying) or spray agglomeration.

The conditions specified below for carrying out the atomization and drying refer to all embodiments of the spraying process which can be carried out in principle, whether normal spray drying, spray granulation or agglomerating spray drying.

The atomization preferably takes place as hydrodynamic atomization as a result of liquid pressure or air pressure via nozzles such as, for example, single-material or multiple-material nozzles or via atomizing disks.

Suitable spraying devices are conventional spray towers into which the polymer dispersion to be atomized is introduced from above. The polymer powders obtained can be discharged at the lower end and be separated off from the drying-gas stream in a downstream cyclone.

Drying gases which can be used are air or inert gases such as nitrogen, argon or helium. The drying gases can be introduced countercurrently or cocurrently to the liquid droplets produced by the atomization through the spraying apparatus. The drying gas is preferably used cocurrently. The entry temperature of the drying gas is kept at least 20° C., preferably at least 40° C., above the glass transition temperature and, according to one embodiment, also at least 20° C., preferably at least 40° C., above the dynamic freezing temperature and at least 20° C., preferably at least 40° C., above the minimum film-forming temperature of the polymer. The entry temperature of the drying gas into the spraying apparatus is particularly preferably kept at 100 to 140° C. and the exit temperature of the drying gas from the spraying apparatus is kept at 45 to 70° C. Very particularly preferably, the entry temperature of the drying gas into the spraying apparatus is kept at 110 to 130° C. and the exit temperature of the drying gas from the spraying device is kept at 50 to 60° C. The exit temperature of the drying gas is very particularly preferably in the same temperature range plus/minus 5° C. as the minimum film-forming temperature.

The evaporation of the water in the spraying apparatus can take place either at atmospheric pressure or at 0.06 to 0.12 MPa.

While carrying out the spraying processes, polymeric spraying auxiliaries such as polyvinyl alcohols, mixtures of polyvinyl alcohol and a graft polymer of polyethylene glycol as graft base and polyvinyl alcohol side chains (commercially available as Kollicoat® Protect), polyvinylpyrrolidones, alkylated and/or hydroxyalkylated celluloses, starch derivatives, lignosulfonates, polyacrylic acids or polyacrylamides can also be added to the aqueous polymer dispersions. Suitable amounts of such spraying auxiliaries are in the range from 0.1 to 30, preferably 1 to 10% by weight, based on the solids content.

Furthermore, antiblocking agents can also be added to the aqueous polymer dispersions. Suitable antiblocking agents are e.g. aluminum silicates such as bentonite, also kieselguhr, colloidal silica, precipitated silica, diatomaceous earth, calcium carbonate, titanium dioxide, zinc oxide, magnesium silicates such as talc or tricalcium phosphate. Suitable amounts of such antiblocking agents are in the range from 0.1 to 15, preferably 0.5 to 5% by weight, based on the solids content.

In principle, customary coating auxiliaries can also be added to the aqueous polymer dispersions. Suitable auxiliaries may be: aroma substances, taste-improving substances, sweetening agents (sugars, sugar alcohols, sweeteners such as e.g. aspartame, saccharine-Na, sodium cyclamate), glidants, wetting agents, release agents, antisticking agents, stabilizers, antioxidants, pore formers, neutralizers, luster agents, dyes, pigments, disinfectants or preservatives, thickeners or plasticizers. Suitable auxiliaries are described e.g. in Fiedler, H. P. Lexikon der Hilfsstoffe für Pharmazie, Kosmetik and angrenzende Gebiete [Lexicon of Auxiliaries for Pharmacy, Cosmetics and Related Fields], 4th edition, Aulendorf: ECV-Editio-Cantor-Verlag, 1996.

Furthermore, the conversion to powder can take place by means of a spray granulation. For this, the aqueous polymer dispersion to be dried is likewise atomized and the droplets produced then come into contact in a fluidized bed with seed particles that have been introduced as initial charge. As a result of this bringing of the seed particles into contact with the droplets of the aqueous polymer dispersion, the seed particles grow to give larger granule particles, with the formation of an onion-peel-like structure around the particle used as seed material.

Conversion to the powder form can also take place with the help of agglomerating spray drying. Here, the polymer dispersion is atomized in a spray tower as described above, where fine dust which is removed from the drying zone is at the same time blown into the atomizing zone, in which the aqueous polymer dispersion is present in the form of fine droplets. The fine dust particles stick together here to give relatively large aggregates with a blackberry-like structure. Additionally, a fluidized bed can also be connected, in which the water content of the particles formed can be further reduced. The resulting aggregates can have particle sizes of from 150 to 1000 µm, preferably from 200 to 500 µm. In this embodiment too, the entry temperature is selected at least 20° C. and preferably at least 40° C. above the glass transition temperature and, according to one embodiment, also at least 20° C., preferably at least 40° C., above the dynamic freezing temperature and at least 20° C., preferably at least 40° C., above the minimum film-forming temperature of the polymer, and the exit temperature of the drying gas from the spraying apparatus is 40 to 85° C., preferably 45 to 70° C. Preferably, the entry temperature of the drying gas into the spraying apparatus is kept at 100 to 140° C. and the exit temperature of the drying gas from the spraying apparatus is kept at 45 to 70° C. Particularly preferably, the entry temperature of the drying gas into the spraying apparatus is kept at 110 to 130° C. and the exit temperature of the drying gas from the spraying apparatus is kept at 50 to 60° C. The blackberry-like structures obtained by spray agglomeration are virtually dust-free and exhibit a particularly advantageous behavior upon redispersion.

In all of the embodiments specified above, spraying auxiliaries such as e.g. aluminum silicates such as bentonite, kieselguhr, colloidal silica, precipitated silica, diatomaceous earth, calcium carbonate, titanium dioxide, zinc oxide, magnesium silicates such as talc or tricalcium phosphate can be blown into the spray tower during the spraying process in amounts of from 0.1 to 15, preferably 0.5 to 5% by weight, based on the polymer powder.

Overall, the particle sizes of the powder formed by spraying processes are governed by the particular variant. In the case of a normal spray drying, particle sizes of from 10 to 150 µm can be achieved. In the case of a spray granulation, such as, for example, a spray fluidized-bed drying, larger particle sizes of from 150 up to 1000 µm can be achieved. In the case of agglomerating spray drying, particle sizes of from 150 to 1000 µm can be achieved.

The copolymers are obtained as free-flowing powders which, for the purposes of the present invention, means that the powders, upon determining the flowability in accordance with DIN ISO 4324 using Pfrengle equipment without stirring aid, flow out of the funnel freely and completely.

The residual solvent content is usually not more than 5% by weight, based on the solids content of the powder.

The redispersible copolymer powders to be used according to the invention for producing the coatings have, in water at a solids content of 20% by weight, low viscosities of preferably less than 300 mPas, particularly preferably less than 200 mPas and in particular less than 100 mPas (values determined by means of Brookfield viscometer at 20° C. and 100 s$^{-1}$). Such viscosities are of particular importance for many applications.

For the purposes of stabilization, the polymer dispersions can be treated, as mentioned, with sparingly water-soluble antioxidants prior to being converted to the powder form. The term "antioxidants" is known per se to the person skilled in the art (see e.g. Römpp-Lexikon der Chemie [Lexicon of Chemistry], 9th edition, 1989, Georg-Thieme-Verlag, Stuttgart) and refers to substances which are intended to inhibit or prevent undesired changes brought about by oxygen or other oxidative processes. According to the invention, suitable antioxidants for stabilizing the coating compositions are sparingly water-soluble antioxidants, i.e. antioxidants whose solubility in water at 20° C. is not more than 1 g/l.

In this connection, suitable antioxidants are primarily the lipophilic substances tocopherol, tocopherol acetate, ascorbyl palmitate, ascorbyl stearate, t-butylhydroquinone, t-butylhydroxyanisole, t-butylhydroxytoluene, octyl gallate or dodecyl gallate or combinations thereof.

Here, the antioxidants used can also be dissolved in an organic solvent. Suitable organic solvents are those solvents which, on the one hand, are miscible with water to a sufficient extent that a concentration of at least 10% by weight in water can be achieved, but, on the other hand, are able to dissolve the sparingly water-soluble antioxidants. Suitable solvents are alcohols such as e.g. ethanol or isopropanol, ketones such as e.g. acetone, methyl ethyl ketone and esters such as e.g. methyl acetate. Usually, these solvents have boiling points below 100° C.

The antioxidants can be brought into organic solution in a manner customary per se. The concentration is selected such that 10 to 1000 g of antioxidant are used per liter of solvent. In total, the amount of organic solvent is selected such that 1 to 20% by weight of solvent are used, based on the weight of the aqueous dispersion.

According to a further embodiment, the antioxidants can be incorporated into the aqueous dispersion in the form of an aqueous micellar solution. For this purpose, the substances are brought into solution in the presence of solubilizing substances ("solubilizers") (as regards the term "solubilization", see Römpp-Chemielexikon, [Chemistry Lexicon], 9th edition). Suitable solubilizers are surfactants such as e.g. sodium docusate or sodium dodecylsulfate, ethoxylated fats, ethoxylated fatty acids, ethoxylated fatty alcohols or polymeric solubilizers.

Suitable polymeric solubilizers are primarily amphiphilic copolymers. According to the invention, amphiphilic copolymers are understood as meaning copolymers which are composed of hydrophilic and hydrophobic segments. The segments can also have a LCST (Lower Critical Solution Temperature). The segments are for their part polymer chains which, on account of their composition and/or the monomers used for producing the segments, are either hydrophilic or hydrophobic. The amphiphilic copolymers can be block polymers or graft polymers. Besides linear block polymers, the structure of the copolymer can also be comb-like or star-like. In the case of the graft polymers, either hydrophobic side chains and a hydrophilic graft base may be present, or hydrophilic side chains and a hydrophobic graft base. The side chains may either be grafted to or grafted on. Suitable amphiphilic copolymers are disclosed for example in WO 2007/017452, WO 2007/051743, WO 2007/065845 and WO 2007/065846, to the description of which with regard to suitable amphiphilic copolymers and their production reference is hereby made. Further amphiphilic copolymers are for example poloxamers.

Suitable hydrophilic segments are N-vinyllactam homopolymer or copolymer chains, in particular N-vinylpyrrolidone-containing polymers, as well as polyvinyl alcohol chains or polyethers. Suitable hydrophobic segments are, for example, homopolymers or copolymers of N-vinyl acetate. A suitable comonomer is for example N-vinylcaprolactam. A preferred polymeric solubilizer is a graft polymer commercially available under the name Soluplus®, BASF SE, with PEG 6000 as graft base and a copolymer side chain produced from vinyl acetate and N-vinylcaprolactam. Also of suitability for producing the micellar solution are all surfactants which have an HLB of more than 12. Such surfactants are described in "Fiedler, Encyclopedia of Excipients", Editio Cantor Verlag. Sixth edition, 2007, pages 112-119. The aqueous antioxidant solubilizates comprise 0.5 to 30% by weight, preferably 1 to 20% by weight, of antioxidant and 1 to 50% by weight, preferably 1 to 30% by weight, of solubilizer. Overall, the amount is selected such that 1 to 40% by weight of aqueous antioxidant solubilizate, based on the weight of the aqueous dispersion, are used.

Furthermore, the sparingly water-soluble antioxidants can be introduced into the aqueous dispersion of the polymeric coating composition in the form of finely divided aqueous dispersions. In this connection, dispersions is the term used to refer to two-phase systems which may be either solid/liquid (suspensions) or liquid/liquid (emulsions). The average particle size (d4,3) of the antioxidants here should be less than 20 µm, preferably less than 10 µm, particularly preferably less than 3 µm.

Thus, the antioxidants can be dissolved in emulsifiers and then dispersed in water. However, the antioxidants can also be added directly to water and be dispersed with the aid of emulsifiers using high-shear dispersing tools. Particular preference is given here to heating the preparation to a temperature above the melting point of the antioxidant, as a result of which an emulsion is formed. This hot emulsion can be added directly to the polymer dispersion with stirring. Alternatively, it can also be cooled beforehand, as a result of which a finely divided suspension is formed. It is particularly preferred to add the hot emulsion to a polymer dispersion which likewise has a temperature above the melting point of the antioxidant.

Suitable emulsifiers are in principle all classes of interface-active substances with an HLB value of >10 (re the Hydrophilic-Lipophilic-Balance value, see Fiedler, Encyclopedia of Excipients, Editio Cantor Verlag Sixth edition, 2007, pages 112-119). Suitable emulsifiers are in principle all ethoxylated fatty acids, ethoxylated fatty alcohols, ethoxylated fatty acid ethers or ethoxylated fatty acid esters with corresponding HLB values. Corresponding ethoxylated sorbitan, stearyl, oleyl, lauryl or palmityl derivatives, for example Solutol® HS (Macrogol 15 hydroxystearate) or ethoxylated hydrogenated castor oil, such as, for example, Cremophor® RH40 (ethoxylated with 40 ethylene oxide units) or the corresponding Eumulgin® grades, for example, are suitable.

Further suitable emulsifiers are poloxamers (polyethylene oxide-polypropylene oxide block copolymers).

The aqueous antioxidant/emulsifier dispersions comprise 1 to 50% by weight, preferably 2 to 30% by weight, of antioxidant and 0.1 to 30% by weight, preferably 0.5 to 10% by weight, of emulsifier.

Overall, the amount is selected such that 1 to 40% by weight of aqueous antioxidant/emulsifier dispersion are used, based on the weight of the aqueous polymer dispersion.

Furthermore, the antioxidants can be used in the form of a so-called "solid solution". The term "solid solution" is known to the person skilled in the art and refers to a molecularly disperse distribution of one solid in another solid. In the present case, the antioxidants can be incorporated as solid solutions into a suitable solid solubilizer or into a polymeric protective colloid. The resulting solid solution can then be incorporated directly in solid form into the aqueous coating composition dispersion, or be converted beforehand into a micellar aqueous solution or into a colloidal solution and then be incorporated into the aqueous coating composition dispersion. The solid solutions can for example be produced by dissolving the antioxidants together with the solubilizer or the protective colloid in a suitable solvent and then evaporating the solvent.

Furthermore, the solid solution of the antioxidants can be prepared by melt extrusion, where antioxidants and solubilizers or polymeric protective colloids are melted together and then extruded, molded and solidified. The granular solid melt extrudates obtained after the extrusion can be incorporated particularly advantageously into the aqueous dispersion of the polymeric coating composition. Suitable matrix polymers and protective colloids for solid solutions here are the amphiphilic copolymers already mentioned, in particular Soluplus®, or poloxamers such as Lutrol® F86, but also nonamphiphilic polymers such as e.g. polyvinylpyrrolidones, vinylpyrrolidone—vinyl acetate copolymers, polyethylene glycols, polyvinyl alcohols, polyvinyl alcohol-polyethylene glycol graft copolymers or hydroxyalkylated celluloses.

Coating compositions can be produced e.g. by intimately mixing a by redispersing the polymer powder obtained according to the invention to give an aqueous polymer dispersion, to which preferably at least one further auxiliary is added.

Suitable additional auxiliaries may be: aroma substances, taste-improving substances, sweetening agents (sugars, sugar alcohols, sweeteners such as e.g. aspartame, saccharine-Na, sodium cyclamate), glidants, wetting agents, release agents, antisticking agents, stabilizers, antioxidants, pore formers, neutralizing agents, luster agents, dyes, pigments, disinfectants or preservatives, thickeners, plasticizers etc. Such substances are described e.g. in Fiedler, H. P. Lexikon der Hilfsstoffe für Pharmazie, Kosmetik and angrenzende Gebiete [Lexicon of Auxiliaries for Pharmacy, Cosmetics and Related Fields], 4th edition, Aulendorf: ECV-Editio-Cantor-Verlag, 1996.

To produce the coating composition, the MMA/DE-AEMA polymer powder can be ground prior to redispersion in water. The grinding can also take place in the presence of the specified additional auxiliaries.

Customary amounts of the auxiliaries are in a range from in each case 0 to 70% by weight, preferably 0 to 60% by weight, in particular 1 to 50% by weight, based on the total weight of the solid of the coating composition.

According to one embodiment of the invention, the coatings are produced with a coating composition according to the invention in aqueous form. The application of the coating composition can take place in aqueous form by granulation, pouring, spreading or by means of spray application.

The coating composition obtained according to the invention can also be applied in powder form to the pharmaceutical dosage forms.

Preferably, the application is as aqueous polymer dispersion obtained by redispersing a pulverulent coating composition according to the invention. In principle, any dispersing apparatus is suitable for the redispersion. Here, the redispersion takes place preferably with the application of low shear forces, preferably by means of a blade, propeller, anchor stirrer or a comparable stirring tool. The polymer powders according to the invention are hereby redispersed spontaneously and rapidly. The redispersion of the polymer powder in water is usually completed in 10 min.

Further components required for producing the coatings can be added to these redispersed preparations. Such components are in particular plasticizers such as e.g. triethyl citrate, tributyl citrate, diethyl sebacate, dibutyl sebacate, acetyl triethyl citrate.

The production of the finely dispersed dispersions by redispersing powders can also take place at very high shear forces such as for example in a rotor-stator apparatus, which is also called Ultra-Turrax, or a colloid mill. The introduction of high shear forces is regulated in a rotor-stator apparatus via the number of revolutions of the apparatus. Preferably, the redispersion takes place with the help of a dispersing apparatus at <5000 rpm. This process is particularly advantageous if further coarsely particulate additives or agglomerated additives additionally have to be incorporated into the dispersion which necessitate a special comminution. The separate comminution of these additives in water and subsequent addition to the redispersed polymer powder is thus dispensed with.

In one particular embodiment, the redispersible polymer powders according to the invention are mixed with further customary coating constituents and/or additives described above to produce so-called ready-to-use preparations which comprise all of the required constituents of a finished coating. These are present in powder or granule form. The user only needs to stir them into water to produce a ready-to-spray suspension. These ready-to-use preparations are produced by dry mixing, grinding, compaction or granulation of the constituents with a granulating liquid, followed by a drying step. Thus, for example, a polymer powder partial neutralized according to the invention can be granulated with an aqueous suspension comprising pigments and optionally further auxiliaries. These granules can then be redispersed to give a spray suspension.

The coating compositions according to the invention can additionally comprise at least one further polymer component. In this connection, mixtures of at least two dispersions, at least one dispersion and at least one solution, at least one dispersion and at least one powder, at least two powders, etc. can be used.

Irrespective of the individual embodiments of the invention, the application amount of the coating composition is preferably in the range from 1 to 20 $mg/cm^2$, preferably 2 to 15 $mg/cm^2$, particularly preferably 4 to 12 $mg/cm^2$.

According to the invention, the coating compositions serve to produce coatings for pharmaceutical dosage forms which are intended to be rapidly releasing in the acidic environment of the stomach, i.e. the coatings according to the invention are soluble in gastric juice. In this connection, rapidly releasing means that at least 80% of the active ingredient has been released after 60 min at 25° C. under atmospheric pressure according to the paddle model (medium: 0.1 N HCl). Coatings obtained according to the invention should not dissolve in the oral cavity and throat in the neutral or almost neutral environment of saliva.

The coatings according to the invention can be used for taste masking or for protecting against moisture. The water vapour permeability of the coatings is very low, as a result of which active ingredients that are sensitive to moisture are protected.

Pharmaceutical dosage forms which can be provided with the coatings according to the invention are tablets, capsules or pellets. Furthermore, active ingredient crystals can also be provided with the coatings according to the invention.

The coating compositions obtained by the process according to the invention are suitable for dosage forms of in principle any desired pharmaceutical active ingredients, which can preferably be administered in isolated or protected form, such as antidepressants, beta receptor blockers, antidiabetic agents, analgesics, antiphlogistics, antirheumatics, antihypotensives, antihypertensives, psychoactive drugs, tranquilizers, antiemetics, muscle relaxants, glucocorticoids, agents for treating ulcerative colitis or Crohn's disease, antiallergic agents, antibiotics, antiepileptics, anticoagulants, antimycotics, antitussives, arteriosclerotic agents, diuretics, enzymes, enzyme inhibitors, gout remedies, hormones and inhibitors thereof, cardiac glycosides, immunotherapeutic agents and cytokines, laxatives, antipanic agents, gastrointestinal therapeutic agents, antimigrane agents, preparation of mineral substances, otologic agents, agents to treat Parkinson's disease, thyroid therapeutic agents, spasmolytics, platelet aggregation inhibitors, vitamins, cytostatics and metastasis inhibitors, phytopharmaceuticals, chemotherapy agents, nutraceuticals, vitamins, carotenoids and amino acids.

Examples of suitable active ingredients are: acarbose, nonsteroidal antirheumatics, cardiac glycosides, acetylsalicylic acid, virustatic agents, aclarubicin, aciclovir, cisplatin, actinomycin, α- and β-sympathomimetics, allopurinol, alosetron, alprostadil, prostaglandins, amantadine, ambroxol, amlodipine, methotrexate, 5-aminosalicylic acid, amitriptyline, amlodipine, amoxicillin, anastrozole, atenolol, atorvastatin, azathioprine, balsalazide, beclomethasone, betahistine, bezafibrate, bicalutamide, diazepam and diazepam derivatives, budesonide, bufexamac, buprenorphine, methadone, calcium salts, potassium salts, magnesium salts, candesartan, carbamazepine, captopril, cephalosporins, celetoxib, cetirizine, chenodeoxycholic acid, ursodeoxycholic acid, theophylline and theophylline derivatives, trypsin, cimetidine, clarithromycin, clavulanic acid, clindamycin, clobutinol, clonidine, cotrimoxazole, codeine, caffeine, vitamin D and derivatives of vitamin D, colestyramine, cromoglycic acid, coumarin and coumarin derivatives, cysteine, cytarabine, cyclophosphamide, cyclosporin, cyproterone, cytarabine, dapiprazole, desogestrel, desonide, dihydralazine, diltiazem, ergot alkaloids, dimenhydrinate, dimethylsulfoxide, dimeticone, dipyridamole, domperidone and domperidone derivatives, donepzil, dopamine, doxazosin, doxorubicin, doxylamine, dapiprazole, benzodiazepine, diclofenac, glycoside antibiotics, desipramine, econazole, ACE inhibitors, enalapril, ephedrine, epinephrin, epoetin and epoetin derivatives, morphinanes, calcium antagonists, irinotecan, modafinil, orlistat, peptide antibiotics, phenytoin, riluzole, risedronate, sildenafil, topiramate, macrolide antibiotics, esomeprazole, estrogen and estrogen derivatives, gestagen and gestagen derivatives, testosterone and testosterone derivatives, androgen and androgen derivatives, ethenzamide, etofenamate, etofibrate, fenofibrate, etofylline, etoposide, famciclovir, famotidine, felodipine, fenofibrate, fentanyl, fenticonazole, gyrase inhibitors, fluconazole, fludarabine, flunarizine, fluorouracil, fluoxetine, flurbiprofen, ibuprofen, flutamide, fluvastatin, follitropin, formoterol, fosfomycin, furosemide, fusidic acid, galantamine, gallopamil, ganciclovir, gemfibrozil, gentamicin, ginkgo, St. John's wort, glibenclamide, urea derivatives as oral antidiabetics, glucagon, glucosamine and glucosamine derivatives, glutathione, glycerol and glycerol derivatives, hypothalamus hormones, goserelin, guanethidine, halofantrine, haloperidol, heparin and heparin derivatives, hyaluronic acid, hydralazine, hydrochlorothiazide and hydrochlorothiazide derivatives, salicylates, hydroxyzine, idarubicin, ifosfamide, imipramine, indometacin, indoramin, insulin, interferons, iodine and iodine derivatives, isoconazole, isoprenaline, glucitol and glucitol derivatives, itraconazole, ketoconazole, ketoprofen, ketotifen, lacidipine, lansoprazole, levodopa, levomethadone, thyroid hormones, lipoic acid and lipoic acid derivatives, lisinopril, lisuride, lofepramine, lomustine, loperamide, loratadine, maprotiline, mebendazole, mebeverine, meclozine, mefenamic acid, mefloquine, meloxicam, mepindolol, meprobamate, meropenem, mesalazine, mesuximide, metamizole, metformin, methotrexate, methylphenidate, methylprednisolone, metixene, metoclopramide, metoprolol, metronidazole, mianserin, miconazole, minocycline, minoxidil, misoprostol, mitomycin, mizolastine, moexipril, morphine and morphine derivatives; evening primrose, nalbuphine, naloxone, tilidine, naproxen, narcotine, natamycin, neostigmine, nicergoline, nicethamide, nifedipine, niflumic acid, nimodipine, nimorazole, nimustine, nisoldipine, adrenaline and adrenaline derivatives, norfloxacin, novamine sulfone, noscapine, nystatin, ofloxacin, olanzapine, olsalazine, omeprazole, omoconazole, ondansetron, orlistat, oseltamivir, oxaceprol, oxacillin, oxiconazole, oxymetazoline, pantoprazole, paracetamol, paroxetine, penciclovir, oral penicillin, pentazocine, pentifylline, pentoxifylline, perphenazine, pethidine, plant extracts, phenazone, pheniramine, barbituric acid derivatives, phenylbutazone, phenytoin, pimozide, pindolol, piperazine, piracetam, pirenzepine, piribedil, piroxicam, pramipexole, pravastatin, prazosin, procaine, promazine, propiverine, propranolol, propyphenazone, prostaglandins, protionamide, proxyphylline, quetiapine, quinapril, quinaprilat, ramipril, ranitidine, reproterol, reserpine, ribavirin, rifampicin, risperidone, ritonavir, ropinirole, rosiglitazone, roxatidine, roxithromycin, ruscogenin, rutoside and rutoside derivatives, sabadilla, salbutamol, salmeterol, scopolamine, selegiline, sertaconazole, sertindole, sertraline, silicates, simvastatin, sitosterol, sotalol, spaglumic acid, sparfloxacin, spectinomycin, spiramycin, spirapril, spironolactone, stavudine, streptomycin, sucralfate, sufentanil, sulbactam, sulfonamides, sulfasalazine, sulpiride, sultamicillin, sultiame, sumatriptan, suxamethonium chloride, tacrine, tacrolimus, taliolol, tamoxifen, taurolidine, tazarotene, tegaserod, temazepam, teniposide, tenoxicam, terazosin, terbinafine, terbutaline, terfenadine, terlipressin, tertatolol, tetracyclines, tetryzoline, theobromine, theophylline, butizine, thiamazole, phenothiazines, thiotepa, tiagabine, tiapride, propionic acid derivatives, ticlopidine, timolol, tinidazole, tioconazole, thioguanine, thioxolone, tiropramide, tizanidine, tolazoline, tolbutamide, tolcapone, tolnaftate, tolperisone, topotecan, torasemide, antiestrogens, tramadol, tramazoline, trandolapril, tranylcypromine, trapidil, trazodone, triamcinolone and triamcinolone derivatives, triamterene, trifluperidol, trifluridine, trimethoprim, trimipramine, tripelennamine, triprolidine, trifosfamide, tromantadine, trometamol, tropalpine, troxerutin, tulobuterol, tyramine, tyrothricin, urapidil, ursodeoxycholic acid, chenodeoxycholic acid, valaciclovir, valdecoxib, valproic acid, vancomycin, vecuronium chloride, venlafaxine, verapamil, vidarabine, vigabatrin, viloxazine, vinblastine, vincamine, vincristine, vindesine, vinorelbine, vinpocetine, viquidil, warfarin, xantinol nicotinate, xipamide, zafirlukast, zalcitabine, zanamivir, zidovudine, zolmitriptan, zolpidem, zopiclone, zotepine and the like.

If desired, the active ingredients can also be used in the form of their pharmaceutically acceptable salts or derivatives, and in the case of chiral active ingredients, both optically active isomers and also racemates or diastereoisomer mixtures can be used. If desired, the compositions according to the invention can also comprise two or more pharmaceutical active ingredients.

According to the invention, the coating compositions can be used for coating extrudates, minitablets, capsules, soft capsules, granules, pellets, micropellets, microcapsules, nanocapsules or crystals.

For producing dosage forms, the coated granules, pellets, micropellets, microcapsules, crystals can be mixed with suitable auxiliaries and compacted to give tablets, which disintegrate in the aqueous environment of the oral cavity and release the coated fine shaped articles again. Of particular importance in this connection are the so-called oral dispersibles, i.e. tablets which disintegrate in the mouth within a short time and release the taste-masked small shaped articles.

Furthermore, the coating compositions can also be used advantageously for coating tablets.

Active ingredient classes and substances which can often bring about an unpleasant bitter taste and can be formulated advantageously according to the invention are e.g.:

analgesics and antirheumatics, such as paracetamol, diclofenac, aceclofenac, ibuprofen, ketoprofen, flurbiprofen, acetylsalicylic acid, levacetylmethadol and oxycodone; psychoactive drugs, such as promethazines, donepezil, modafinil, nefazodone, reboxetine, sertindole and sertraline;

antibiotics, such as erythromycin, roxithromycin, clarithromycin, grepafloxacin, ciprofloxacin, levofloxacin, sparfloxacin, trovafloxacin and nevirapine;

beta blockers, such as propranolol, metoprolol, bisoprolol and nebivolol;

antidiabetics, such as metformin, miglitol and repaglinide;

$H_1$ antihistamines, such as diphenhydramine, fexofenadine and mizolastine;

$H_2$ antihistamines, such as cimetidine, famotidine, roxatidine, nizatidine, ticlopidine, cetirizine and ranitidine;

vitamins such as thiamine nitrate and quinidine sulfate, amyloprilose HCl, pseudoephedrine HCl, sildenafil, topiramate, granisetron, rebamipide, quinine HCl, etc.

Also various salts of these active ingredients can be formulated correspondingly.

The exceptional taste masking results from the insolubility of the polymers according to the invention at pH values greater than 6 and the rapid solubility at pH values below 6. That is, in the saliva (pH: 7.2) correspondingly coated forms are stable for a very long time and there is no contact between the bitter drug and the oral mucosa, but in the stomach at pH values from 1 to 5 there is very rapid release of the active ingredient. The dissolution is so rapid here that there is no difference in the onset of action compared with an uncoated form. As a rule, film coatings of a polymer according to the invention dissolve within 5 min in gastric juice, whereas in phosphate buffer pH 7.2 they are stable for 2 hours. Surprisingly, the film coatings also dissolve relatively quickly in media with pH values of 4.5, meaning that the administration forms produced therefrom develop a rapid effect even in anacidic patients or patients which are treated with antacids. These exceptional application properties of the coating compositions are also retained after the conversion to powders and redispersion or melting of the powders.

EXAMPLES

Abbreviations Used

Glass tramsition temperature: Tg

Demin. water: demineralized water

In all examples, the polymer used was a polymer referred to as polymer A. The preparation of polymer A was carried out analogously to example 1 WO 2009/016258.

Polymer A methyl methacrylate/diethylaminoethyl methacrylate, weight ratio 55:45, K value 49, Tg 57° C.

The K value was measured at 0.1% strength by weight in NMP. The polymer was used as aqueous dispersion with a pH of 9+/−0.3 or used as spray-dried powder. The average particle size of the primary dispersion was 127 nm. The glass transition temperatures were determined by means of DSC at a heating rate of 20° K/min. The minimum film-forming temperature corresponded to the Tg within the scope of the measurement accuracy of plus/minus 5° C.

When determining the average particle sizes of the powders, the D(4,3) value was determined by means of light diffraction using a Malvern Mastersizer 2000.

When determining the average particle sizes of the redispersed powders by means of light scattering, the value was determined using a "Malvern Zetasizer nano S" as Z-Average value.

Auxiliaries Used:

Ludipress®: free-flowing granules comprising 94.4% by weight of lactose, 3.2% by weight of Kollidon 30 (USP) and 3.4% by weight of Kollidon CL (USP)

Kollidon® CL-F: Crospovidone

Avicel® PH102: microcrystalline cellulose, average particle diameter 100 μm

Simethicone: CTFA name for a mixture of dimethicone with an average chain length of 200-350 dimethylsiloxane units and silica gel Aerosil® 200: finely divided silica

Example 1 (Comparative Example)

1000 ml of an aqueous dispersion of polymer A with a solids content of 30% by weight were mixed, with stirring, with 6.5 g of 85% strength by weight phosphoric acid. This corresponds a degree of neutralization of 8 mol %. This partially neutralized spray suspension was spray-dried in a spray tower. Atomization was carried out here via a 1.4 mm two-material nozzle with an atomization pressure of 3.0 bar. The drying gas was passed tangentially in the input area of the spray dryer and the dried product was separated off in a cyclone. The inlet air temperature was 107° C. and the outlet air temperature 56° C. The average particle size of the powder was 30 μm. 100 g of the spray-dried product were dispersed in water to give a spray suspension with 20% solids content by stirring with a paddle stirrer for 60 min. Measurement of the particle size by means of light scattering showed a bimodal distribution with a maximum both at 130 nm and at 450 nm.

The preparation prepared in this way was admixed with 14 g of acetyl triethyl citrate, stirred for two hours and applied to tablet cores by spraying.

TABLE 1

| Core composition: | | |
|---|---|---|
| Composition | [%] | [mg] |
| Caffeine, gran. 0.2-0.5 mm | 15.15 | 50 |
| Ludipress | 72.43 | 239 |
| Avicel PH 101 | 12.12 | 40 |
| Magnesium stearate | 0.3 | 1 |
| | 100.00 | 330 |

To produce the cores, the weighed constituents caffeine, Ludipress and Avicel PH 101 were mixed in a Diosna mixer for 3 minutes at stage 1. After adding magnesium stearate, mixing was carried out for a further 1 minute. The powder mixture prepared in this way was compressed on a rotary press to give tablets with a weight of 330 mg and a breaking strength of 80 N.

TABLE 2

| Spraying conditions: | |
|---|---|
| Equipment | Innojet Ventilus 1<br>Nozzle: IRN 2 |
| Inlet air temperature | 60° C. |
| Inlet air amount | 90 m³/h |
| Batch size | 150 g |
| Spraying rate | 1.5 g/min |
| Spraying pressure | 0.15 MPa |
| Application amount | 4 mg/cm² |

Testing as to the resistance of the coated tablets in buffer pH 6.8 was carried out by means of six-fold determination in a release apparatus (USP, Apparatus 2).

The resistance of the tablets (active ingredient release <2%) was determined after 30, 60, 90 and 120 min.

The tablets produced in this way exhibited no resistance in buffer pH 6.8.

Example 2 (Comparative Example)

5.1 g of oxalic acid were dissolved in 500 ml of demin. water and then incorporated, with stirring, into 1000 ml of an aqueous dispersion of polymer A with a solids content of 30% by weight. This corresponds to a degree of neutralization of 8 mol %, This partially neutralized spray suspension was spray-dried analogously to example 1 in a spray tower.

The average particle size of the powder was 35 μm.

The powder was redispersed analogously to example 1 and shows a monomodal distribution with a maximum at 180 nm.

Further processing to give film tablets with an application amount of 4 mg/cm² was carried out analogously to example 1. The tablets produced in this way exhibited no resistance in buffer pH 6.8 despite very good redispersion.

Example 3

6.7 g of succinic acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized spray suspension was spray-dried analogously to example 1 in a spray tower.

The average particle size of the powder was 34 μm.

The powder was redispersed analogously to example 1 and shows a monomodal distribution with a maximum at 170 nm.

Further processing to give film tablets with an application amount of 4, 8 and 12 mg/cm² was carried out analogously to example 1.

Testing the tablets as to resistance in buffer pH 6.8 revealed the following results:

|  | 4 mg/cm² | 8 mg/cm² | 12 mg/cm² |
| --- | --- | --- | --- |
| 30 min | 100% | 100% | 100% |
| 60 min | 72% | 95% | 100% |

Example 4 (Comparative Example)

12.1 g of sodium dihydrogen citrate were dissolved in 500 ml of demin. water and then incorporated, with stirring, into 1000 ml of an aqueous dispersion of polymer A with a solids content of 30% by weight. This corresponds to a degree of a neutralization of 8 mol %. This partially neutralized spray suspension was spray-dried analogously to example 1 in a spray tower.

The average particle size of the powder was ca. 32 μm.

The powder was redispersed analogously to example 1 and exhibited a bimodal distribution of the particle sizes with a maximum both at 197 nm and at 520 nm.

TABLE 3

| Core composition: | | |
| --- | --- | --- |
| Composition | [%] | [mg] |
| Propranolol-HCl | 13.4 | 40.0 |
| Ludipress ® | 40.2 | 120.7 |
| Avicel ® PH 102 | 40.2 | 120.7 |
| Kollidon ® VA 64 | 5.2 | 15.6 |
| Magnesium stearate | 1.0 | 3.0 |
|  | 100.00 | 300 |

To produce the cores, the weighed constituents propranolol-HCl, Ludipress, Avicel PH 102 and Kollidon VA 64 were mixed in a Diosna mixer for 3 minutes at stage 1. After adding magnesium stearate, mixing was carried out for a further 1 minute. The powder mixture prepared in this way was compressed on a rotary press to give tablets with a weight of 300 mg and a breaking strength of 85 N.

Further processing to give film tablets with an application amount of 4 mg/cm² was carried out analogously to example 1.

The film tablets produced in this way exhibited no resistance in buffer pH 6.8.

Example 5 (Comparative Example)

168.5 ml of 1 molar sulfuric acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized spray suspension was spray-dried analogously to example 1 in a spray tower.

The average particle size of the powder was ca. 37 μm.

The powder was redispersed analogously to example 1 and shows a monomodal distribution with a maximum at 192 nm.

Further processing to give film tablets with an application amount of 4 mg/cm² was carried out analogously to example 1. The tablets produced in this way surprisingly exhibited no resistance in buffer pH 6.8 despite very good redispersion.

Example 6

7.4 g of glutaric acid were dissolved in 500 ml of demin. water and then incorporated, with stirring, into 1000 ml of an aqueous dispersion of polymer A with a solids content of 30%. This corresponds to a degree of neutralization of 8 mol %. This partially neutralized spray suspension was spray-dried analogously to example 1 in a spray tower.

The average particle size of the powder was ca. 32 μm.

The powder was redispersed analogously to example 1 and shows a monomodal distribution with a maximum at 178 nm.

Further processing to give film tablets with an application amount of 4, 8 and 12 mg/cm² was carried out analogously to example 1.

Testing the tablets as to resistance in buffer pH 6.8 revealed the following results:

|  | 4 mg/cm² | 8 mg/cm² | 12 mg/cm² |
| --- | --- | --- | --- |
| 30 min | 100% | 100% | 100% |
| 60 min | 68% | 91% | 100% |

Example 7 (Comparative Example)

15.9 g of stearic acid were dissolved in 500 ml of demin. water and then incorporated, with stirring, into 1000 ml of an aqueous dispersion of polymer A with a solids content of 30%. This corresponds to a degree of neutralization of 8 mol %. This partially neutralized spray suspension was spray-dried analogously to example 1 in a spray tower.

The average particle size of the powder was ca. 43 µm.

The powder was redispersed analogously to example 1. The measurement of the distribution revealed no result since the redispersion was completely unsatisfactory.

Further processing to give film tablets was not possible.

Example 8 (Comparative Example)

3.4 ml of acetic acid were dissolved in 500 ml of demin. water and then incorporated, with stirring, into 1000 ml of an aqueous dispersion of polymer A with a solids content of 30%. This corresponds to a degree of neutralization of 8 mol %. This partially neutralized spray suspension was spray-dried analogously to example 1 in a spray tower.

The average particle size of the powder was ca. 41 µm.

The powder was redispersed analogously to example 1 and shows a monomodal distribution with a maximum at 191 nm.

TABLE 4

Core composition:

| Composition | [%] | [mg] |
|---|---|---|
| Quinine hydrochloride dihydrate | 30.30 | 100.00 |
| Ludipress | 57.27 | 189.00 |
| Avicel PH 102 | 12.02 | 39.67 |
| Aerosil ® 200 | 0.11 | 0.33 |
| Magnesium stearate | 0.30 | 1.00 |
| | 100.00 | 330 |

To produce the cores, the weighed constituents quinine HCl, Ludipress, Avicel PH 102 and Aerosil 200 were mixed in a Diosna mixer for 3 minutes at stage 1. After adding magnesium stearate, mixing was carried out for a further 1 minute. The powder mixture prepared in this way was compacted on a rotary press to give tablets with a weight of 330 mg and a breaking strength of 80 N.

Further processing to give film tablets with an application amount of 4 mg/cm² was carried out analogously to example 1. The tablets produced in this way surprisingly exhibited no resistance in buffer pH 6.8 despite very good redispersion.

Example 9

6.5 g of fumaric acid were dissolved in 500 ml of demin. water and then incorporated, with stirring, into 1000 ml of an aqueous dispersion of polymer A with a solids content of 30%. This corresponds to a degree of neutralization of 8 mol %. This partially neutralized spray suspension was spray-dried analogously to example 1 in a spray tower.

The average particle size of the powder was ca. 39 µm.

The powder was redispersed analogously to example 1 and shows a monomodal distribution with a maximum at 183 nm.

Further processing to give film tablets with an application amount of 4, 8 and 12 mg/cm² was carried out analogously to example 1.

Testing the tablets as to resistance in buffer pH 6.8 revealed the following results:

| | 4 mg/cm² | 8 mg/cm² | 12 mg/cm² |
|---|---|---|---|
| 30 min | 100% | 100% | 100% |
| 60 min | 65% | 87% | 100% |

Example 10

6.5 g of fumaric acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized dispersion was spray-dried in a FSD spray tower, with atomization taking place via a 1.4 mm two-material nozzle at an atomization pressure of 0.3 MPa. The inlet air temperature was 110° C. and the outlet air temperature was 57° C. The fines fraction was separated off during the spray drying and blown again in front of the spray nozzle so that spray-dried particles with an average particle size of 280 µm resulted.

The spray-dried product was redispersed in water to give a spray suspension with 20% by weight solids content by stirring with a paddle stirrer for 60 min. Measurement of the particle size by means of light scattering revealed a value of 175 nm.

The preparation prepared in this way was admixed with 14 g of acetyl triethyl citrate, stirred for two hours and applied by spraying to tablet cores (formulation table 1) analogously to example 1.

Testing the tablets with an application amount of 4 mg/cm² as to resistance in buffer pH 6.8 revealed the following results

| 30 min | 100% |
|---|---|
| 60 min | 71% |

Example 11

6.7 g of succinic acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized dispersion was spray-dried analogously to example 10 in a FSD spray tower. The average particle size of the powder was ca. 312 µm.

The spray-dried product was redispersed in water to give a spray suspension with 20% by weight solids content by stirring with a paddle stirrer for 60 min. Measurement of the particle size by means of light scattering revealed a value of 172 nm.

The preparation prepared in this way was admixed with 14 g of acetyl triethyl citrate, stirred for two hours and applied by spraying to tablet cores analogously to example 4 (table 3).

Testing the tablets with an application amount of 4 mg/cm² as to resistance in buffer pH 6.8 revealed the following results

| 30 min | 100% |
|---|---|
| 60 min | 75% |

Example 12

7.4 g of glutaric acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized dispersion was spray-dried analogously to example 10 in a FSD spray tower. The average particle size of the powder was 295 μm.

The spray-dried product was redispersed in water to give a spray suspension with 20% by weight solids content by stirring with a paddle stirrer for 60 min. Measurement of the particle size by means of light scattering revealed a value of 188 nm.

The preparation prepared in this way was admixed with 14 g of acetyl triethyl citrate, stirred for two hours and applied by spraying to tablet cores analogously to example 8 (table 4).

Testing the tablets with an application amount of 4 mg/cm$^2$ as to resistance in buffer pH 6.8 revealed the following results

| | |
|---|---|
| 30 min | 100% |
| 60 min | 72% |

Example 13

1000 ml of an aqueous dispersion of polymer A with a solids content of 30% by weight was spray-dried in a FSD spray tower, the atomization taking place via a 1.4 mm two-material nozzle at an atomization pressure of 0.3 MPa. The inlet air temperature was 127° C. and the outlet air temperature 59° C. The fines fraction was separated off during the spray drying and blown again in front of the spray nozzle such that spray-dried particles with an average particle size of 220 μm resulted.

5.2 g of fumaric acid were dissolved in 1000 ml of demin. water and then 250 g of the spray-dried powder were incorporated with stirring using a paddle stirrer. This corresponds to a degree of neutralization of 8 mol %. After a redispersion time of 60 min, the average particle size was 184 nm.

The preparation prepared in this way was admixed with 35 g of acetyl triethyl citrate, stirred for two hours and applied by spraying to tablet cores (formulation table 3) analogously to example 1.

Testing the tablets with an application amount of 4 mg/cm$^2$ as to resistance in buffer pH 6.8 revealed the following results

| | |
|---|---|
| 30 min | 100% |
| 60 min | 68% |

Example 14

5.3 g of succinic acid were dissolved in 1000 ml of demin. water and then 250 g of the spray-dried powder from example 13 were incorporated with stirring using a paddle stirrer. This corresponds to a degree of neutralization of 8 mol %. After a redispersion time of 60 min, the average particle size was 165 nm.

The preparation prepared in this way was admixed with 35 g of acetyl triethyl citrate, stirred for two hours and applied by spraying to tablet cores (formulation table 4) analogously to example 1.

Testing the tablets with an application amount of 4 mg/cm$^2$ as to resistance in buffer pH 6.8 revealed the following results

| | |
|---|---|
| 30 min | 100% |
| 60 min | 79% |

Example 15

5.9 g of glutaric acid were dissolved in 1000 ml of demin. water and then 250 g of the spray-dried powder from example 13 were incorporated with stirring using a paddle stirrer. This corresponds to a degree of neutralization of 8 mol %. After a redispersion time of 60 min, the average particle size was 174 nm.

The preparation prepared in this way was admixed with 35 g of acetyl triethyl citrate, stirred for two hours and applied by spraying to tablet cores (formulation table 1) analogously to example 1.

Testing the tablets with an application amount of 4 mg/cm$^2$ as to resistance in buffer pH 6.8 revealed the following results

| | |
|---|---|
| 30 min | 100% |
| 60 min | 69% |

Example 16

6.5 g of fumaric acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized dispersion was spray-dried analogously to example 10 in a FSD spray tower. The average particle size of the powder was 280 μm.

The spray-dried product was redispersed in water to give a spray suspension with 20% by weight solids content by stirring using a paddle stirrer for 60 min Measurement of the particle size by means of light scattering revealed a value of 175 nm.

The preparation prepared in this way was admixed with 14 g of acetyl triethyl citrate, stirred for two hours and applied to caffeine pellets by spraying analogously to example 1.

TABLE 5

| Composition of pellets: | |
|---|---|
| Composition | [% by weight] |
| Caffeine | 20.0 |
| Lactose | 38.5 |
| Microcrystalline | 38.5 |
| Kollidon ® CL-F | 3.0 |
| | 100.00 |

The constituents were mixed in a Diosna mixer for 3 min and then wetted with water. This wet mass was extruded and then rounded in a rounding machine to give pellets with a diameter of 0.7-1.4 mm.

Testing the pellets with an application amount of 4 mg/cm² as to resistance in buffer pH 6.8 revealed the following results

| | |
|---|---|
| 30 min | 100% |
| 60 min | 87% |

Example 17

6.7 g of succinic acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized dispersion was spray-dried analogously to example 10 in a FSD spray tower. The average particle size of the powder was 312 μm.

The spray-dried product was redispersed in water to give a spray suspension with 20% by weight solids content by stirring using a paddle stirrer for 60 min Measurement of the particle size by means of light scattering revealed a value of 172 nm.

The preparation prepared in this way was admixed with 14 g of acetyl triethyl citrate, stirred for two hours and applied by spraying to theophyllin granules (particle size from 0.2-0.7 mm) analogously to example 1.

Testing the granules with an application amount of 4 mg/cm² as to resistance in buffer pH 6.8 revealed the following results

| | |
|---|---|
| 30 min | 100% |
| 60 min | 91% |

Example 18

7.4 g of glutaric acid were dissolved in 500 ml of demin. water and then incorporated, with stirring, into 1000 ml of an aqueous dispersion of polymer A with a solids content of 30% by weight. This corresponds to a degree of neutralization of 8 mol %. This partially neutralized dispersion was spray-dried analogously to example 10 in a FSD spray tower. The average particle size of the powder was 295 μm.

The spray-dried product was redispersed in water to give a spray suspension with 20% by weight solids content by stirring with a paddle stirrer for 60 min. Measurement of the particle size by means of light scattering revealed a value of 188 nm.

The preparation prepared in this way was admixed with 14 g of acetyl triethyl citrate, stirred for two hours and applied by spraying to paracetamol crystals (diameter 0.3 mm) analogously to example 1 by spraying.

Testing the granules with an application amount of 4 mg/cm² as to resistance in buffer pH 6.8 revealed the following results

| | |
|---|---|
| 30 min | 100% |
| 60 min | 90% |

Example 19

27.6 g of sodium lauryl sulfate and 14.7 g of fumaric acid were dissolved in 1500 ml of demin water and then incorporated, with stirring, into 3000 ml of an aqueous dispersion of polymer A with a solids content of 30% by weight. This corresponds to a degree of neutralization of 6 mol %. This partially neutralized spray suspension was spray-dried in a spray tower. The atomization was carried out here via a 1.4 mm two-material nozzle with an atomization pressure of 0.3 MPa. The drying gas was passed tangentially in the input region of the spray dryer and the dried product was separated off in a cyclone. The inlet air temperature was 112° C. and the outlet air temperature 59° C. The average particle size of the powder was 37 μm. 750 g of the spray-dried powder was redispersed in demin. water to give a spray suspension with 20% by weight solids content by stirring for 60 minutes using a propeller stirrer. Measurement of the particle size by means of light scattering showed a monomodal distribution with a maximum at 173 nm. The spray suspension was admixed with 13% by weight of tributyl citrate based on solid polymer and, after stirring for two hours, further processed with the parameters listed in table 5.

TABLE 5

| Spray conditions: | |
|---|---|
| Equipment | Manesty |
| Inlet air temperature | 60° C. |
| Inlet air amount | 450 m³/h |
| Drum speed | 14 rpm |
| Batch size | 5 kg |
| Core | Example 1 |
| Spraying rate | 25 g/min |
| Atomization pressure | 0.28 MPa |
| Spray width | 0.28 MPa |
| Application amount | 4 mg/cm² |

Testing the tablets as to resistance in buffer pH 6.8 revealed the following results:

| | |
|---|---|
| 30 min | 100% |
| 60 min | 69% |

Example 20

Powder A:

1000 ml of an aqueous dispersion of polymer A with a solids content of 30% by weight were spray-dried in a spray tower. Atomization was carried out here via a 1.4 mm two-material nozzle with 0.3 MPa atomization pressure. The drying gas was passed tangentially in the input area of the spray dryer and the dried product was separated off in a cyclone. The inlet air temperature was 109° C. and the outlet air temperature 58° C. The average particle size of the powder was 33 μm.

Powder B:

105.1 g of tartaric acid were dissolved in 500 ml of demin. water and then incorporated, with stirring, into 1000 ml of an aqueous dispersion of the polymer with a solids content of 30% by weight. This corresponds to a degree of neutralization of 100 mol %. This spray suspension was spray-dried in a spray tower analogously to powder A.

The average particle size of the powder was 35 μm.

Powder A was mixed with powder B in a Turbula such that a degree of neutralization of 7 mol % was established and then redispersed in demin. water with stirring using paddle stirrers to give a 20% strength by weight dispersion.

Measurement of the particle size by means of light scattering showed a monomodal distribution with a maximum at 168 nm. After adding 13% by weight of acetyl triethyl citrate based on polymer, the spray suspension was sprayed analogously to example 19 on caffeine cores as per table 1.

Testing the tables with an application amount of 4 mg/cm$^2$ as to resistance in buffer pH 6.8 revealed the following results

| | |
|---|---|
| 30 min | 100% |
| 60 min | 72% |

Example 21

14.2 g of sebacic acid were suspended in 500 ml of demin. water and then incorporated, stirring, into 100 ml of an aqueous dispersion of polymer A with a solids content of 30% by weight. This corresponds to a degree of neutralization of 100 mol %.

This solution was incorporated, with stirring, into 1300 ml of an aqueous dispersion of the polymer with a solids content of 30% by weight such that a degree of neutralization of 7 mol % was established. The spray suspension prepared in this way was spray-dried in a FSD spray tower, the atomization taking place via a 1.4 mm two-material nozzle at an atomization pressure of 0.3 MPa. The inlet air temperature was 118° C. and the outlet air temperature was 63° C. The fines fraction was separated off during the spray drying and blown again in front of the spray nozzle such that spray-dried particles with an average particle size of 263 µm resulted. 100 g of the spray-dried product was dispersed in water to give a spray suspension with 20% by weight of solids content by stirring with a paddle stirrer for 60 min Measurement of the particle size by means of light scattering showed a monomodal distribution with a maximum at 178 nm.

The preparation prepared in this way was admixed with 15% by weight of acetyl triethyl citrate based on solid polymer, stirred for two hours and applied analogously to example 19 by spraying to tablet cores as per table 4.

Testing the tablets with an application amount of 4 mg/cm$^2$ as to resistance in buffer pH 6.8 revealed the following results:

| | |
|---|---|
| 30 min | 100% |
| 60 min | 78% |

Example 22

50 g of PEG 6000, 200 g of talc, 9 g of titanium dioxide and 9 g of iron oxide red were mixed in a Turbula mixer and then ground in a pin mill. This mixture was suspended in 250 g of demin. water and applied to 500 g of polymer powder prepared according to example 10 by means of Diosna granulation such that granules with an average particle size of 187 µm result.

TABLE 6

| Granulation conditions: | |
|---|---|
| Equipment | Diosna |
| Mixer rotational speed | 350 rpm |
| Chopper rotational speed | 2000 rpm |

100 g of these granules were dispersed in water to give a spray suspension with 20% by weight solids content by stirring with a paddle stirrer for 60 min Measuring the particle size by means of light scattering showed a monomodal distribution with a maximum at 177 nm.

The preparation prepared in this way was admixed with 15% by weight of acetyl triethyl citrate based on solid polymer, stirred for two hours and applied analogously to example 1 by spraying to tablet cores as per table 3.

Testing the tablets with an application amount of 4 mg/cm$^2$ as to resistance in buffer pH 6.8 revealed the following results:

| | |
|---|---|
| 30 min | 100% |
| 60 min | 82% |

Example 23

500 g of polymer powder prepared according to example 11 were mixed with 3 g of lecithin, 6 g of stearic acid and 150 g of talc in a Turbula mixer and then further processed by means of a compactor. The flakes produced in this way were ground and then redispersed in demin. water. Measuring the particle size by means of light scattering showed a monomodal distribution with a maximum at 181 nm.

2.5% by weight of BHT were dissolved in 15% by weight of acetyl triethyl citrate (based on solid polymer) and then added to the dispersion.

The preparation prepared in this way was admixed with 15% by weight of acetyl triethyl citrate based on solid polymer, stirred for two hours and applied analogously to example 1 by spraying to tablet cores as per table 1.

Testing the tablets with an application amount of 4 mg/cm$^2$ as to resistance in buffer pH 6.8 revealed the following results.

| | |
|---|---|
| 30 min | 100% |
| 60 min | 84% |

Example 24

200 g of talc and 8 g of indigotin lake were suspended in 500 g of demin. water and then applied to 500 g of polymer powder prepared according to example 12 in a fluidized-bed process.

TABLE 7

| Granulation conditions: | |
|---|---|
| Equipment | Glatt GPC 1 |
| Inlet air temperature | 60° C. |
| Inlet air amount | 300 m$^3$/h |

TABLE 7-continued

| Granulation conditions: | |
|---|---|
| Equipment | Glatt GPC 1 |
| Batch size | 500 g |
| Spraying pressure | 0.15 MPa |

The average particle size of the granules was ca. 312 µm.

100 g of the granules were redispersed in demin. water to give a spray suspension with 20% by weight of solids content by stirring for 60 min with a propeller stirrer. Measurement of the particle size by means of light scattering showed a monomodal distribution with a maximum at 193 nm. The spray suspension was admixed with 13% by weight of tributyl citrate based on solid powder and, after stirring for two hours, further processed analogously to example 19 by spraying onto tablet cores according to table 4.

For an application amount of 4 mg/cm$^2$, 74% of the coated tablets exhibited a resistance of 100% after 30 min.

Example 25

200 g of talc, 8 g of indigotin lake and 11.9 g of glutaric acid were suspended in 500 g of demin. water and then applied to 500 g of polymer powder prepared according to example 13 in a fluidized-bed process analogously to example 11. This corresponds to a degree of neutralization of 8 mol %.

The average particle size of the granules was 298 µm.

100 g of the granules were redispersed in demin. water to give a spray suspension with 20% by weight solids content by stirring for 60 min using a propellor stirrer. Measurement of the particle size by means of light scattering showed a monomodal distribution with a maximum at 184 nm. The spray suspension was admixed with 13% by weight of tributyl citrates, based on solid polymer, and, after stirring for two hours, was further processed analogously to example 1 by spraying onto tablet cores as per table 3.

For an application amount of 4 mg/cm$^2$, the coated tablets exhibited a resistance of 83% after 60 min.

Example 26

100 g of talc, 20 g of iron oxide red and 5.2 g of malonic acid were suspended in 300 g of demin. water and then homogenized by means of an Ultra-Turrax for 15 min at 10000 rpm. This pigment suspension was incorporated, with stirring, into 1000 ml of an aqueous dispersion of polymer A with a solids content of 30% by weight. The spray suspension prepared in this way and having a degree of neutralization of 7 mol % was then spray-dried in a SBD spray tower, atomization taking place via a 1.4 mm two-material nozzle at an atomization pressure of 0.30 MPa. The inlet air temperature was 135° C. and the outlet air temperature 63° C. The fines fraction was separated off during the spray-drying and blown again in front of the spray nozzle such that spray-dried particles with an average particle size of 320 µm resulted. The spray-dried product was incorporated in water to give a spray suspension with a solids content of 20% by weight by stirring using a paddle stirrer. The preparation prepared in this way was admixed with 15% triethyl citrate based on solid polymer, stirred for a further two hours and applied by spraying to tablet cores (table 1) analogously to example 1.

The coated tablets with an application amount of 4 mg/cm$^2$ exhibited a resistance of 100% after 60 min in buffer pH 6.8.

Example 27

100 g of polymer powder prepared according to example 10 were mixed with 50 g of talc and 4 g of indigotin lake in a Turbula mixer.

Redispersing this preparation in water to give a 20% strength by weight suspension using a paddle stirrer produced a particle size of 182 nm. The suspension was admixed with 15% by weight of dibutyl sebacate and, after stirring for two hours, sprayed onto tablets according to table 4 analogously to example 1. For an application amount of 4 mg/cm$^2$, the coated tablets exhibited a resistance of 100% after 30 min and a resistance of 78% after 60 min.

Example 28

100 g of polymer powder prepared according to example 13 were mixed with 50 g of very finely ground talc, 4 g of indigotin lake and 2.3 g of sebacic acid in a Turbula mixer.

After redispersing this preparation in water to give a 20% strength by weight suspension with a degree of neutralization of 5 mol % by means of a paddle stirrer, the particle size was 175 nm. The suspension was admixed with 15% by weight of dibutyl sebacate and 0.5% Simethicon® and, after stirring for two hours, sprayed analogously to example 1 onto tablets according to table 4. For an application amount of 4 mg/cm$^2$, the coated tablets exhibited a resistance of 100% after 30 min.

Example 29

100 g of polymer powder prepared according to example 11 were mixed with 60 g of talc, 6 g of iron oxide red and 0.5 g of lecithin in a Turbula mixer and then ground in a pin mill. Redispersion of this preparation in water to give a 20% strength by weight suspension by means of a paddle stirrer produced a particle size of 176 nm, talc and ion oxide having been centrifuged off beforehand for this determination.

The suspension was admixed with 15% by weight of dibutyl sebacate and, after stirring for two hours, sprayed analogously to example 19 onto tablets according to table 1. For an application amount of 4 mg/cm$^2$, the coated tablets exhibited a resistance of 83% after 60 min.

Example 30

1000 ml of an aqueous dispersion of polymer A with a solids content of 30% by weight were spray-dried in an SBD spray tower, the atomization taking place via a 1.4 mm two-material nozzle at an atomization pressure of 0.3 MPa. The inlet air temperature was 110° C. and the outlet air temperature 57° C. The fines fraction was separated off during the spray-drying and blown again in front of the spray nozzle such that spray-dried particles with an average particle size of 190 µm resulted.

30 g of titanium dioxide, 200 g of talc, 8.4 g of adipic acid and 25 g of iron oxide were ground in a pin mill, then mixed with the spray-dried powder and redispersed in demin. water to give a spray suspension with 20% by weight solids content by stirring using a paddle stirrer for 60 min Measurement of the particle size by means of light scattering produced a value of 170 nm.

The preparation prepared in this way was admixed with 15% by weight of triethyl citrate, based on solid polymer, stirred for two hours and applied analogously to example 19 by spraying onto tablet cores according to table 1.

Testing the tablets as to resistance in buffer pH 6.8 revealed the following results:

| 30 min | 100% |
|---|---|
| 60 min | 76% |

Example 31

1000 ml of an aqueous dispersion of polymer A with a solids content of 30% by weight were spray-dried in a spray tower, the atomization taking place via a 1.4 mm two-material nozzle at an atomization pressure of 0.3 MPa. The inlet air temperature was 112° C. and the outlet air temperature 58° C.

This powder was mixed with 8.4 g of finely powdered adipic acid, 60 g of fine talc, 2 g of fine xanthan, 15 g of fine iron oxide red and then redispersed with stirring in water to give a spray suspension with 20% solids content by stirring using a paddle stirrer for 60 min. Measurement of the particle size by means of light scattering produced a value of 168 nm, talc and iron oxide having been centrifuged off beforehand for this determination.

The preparation prepared in this way was admixed with 15% by weight of triethyl citrate, based on solid polymer, stirred for two hours and applied analogously to example 19 by spraying onto tablet cores according to table 1.

Testing the tablets as to resistance in buffer pH 6.8 revealed the following results.

| 30 min | 100% |
|---|---|
| 60 min | 79% |

Example 32

1000 ml of an aqueous dispersion of polymer A with a solids content of 30% by weight were spray-dried in an FSD spray tower, the atomization taking place via a 1.4 mm two-material nozzle at an atomization pressure of 0.3 MPa. The inlet air temperature was 123° C. and the outlet air temperature 54° C. The fines fraction was separated off during the spray-drying and blown again in front of the spray nozzle such that spray-dried particles with an average particle size of 211 μm resulted.

15.1 g/37.7 g/75.5 g of malic acid were dissolved in each case in 1000 ml of demin. water and then 250 g of the spray-dried powder were incorporated, with stirring, into the respective malic acid solution using a paddle stirrer. This corresponds to a degree of neutralization of 2, 5 or 10 mol %. After a redispersion time of 60 min, the average particle size of the respective dispersions was 220/198/182 nm.

The preparation prepared in this way was admixed with 35 g of acetyl triethyl citrate, stirred for two hours and applied analogously to example 1 by spraying onto tablet cores according to table 3.

Testing the tablets with an application amount of 4 mg/cm$^2$ as to resistance in buffer pH 6.8 revealed the following results.

|  | 2 mol % | 5 mol % | 10 mol % |
|---|---|---|---|
| 30 min | 100% | 100% | 100% |
| 60 min | 37% | 65% | 89% |

Example 33

1.3 g of succinic acid, 1.2 g of fumaric acid and 1.6 g of tartaric acid were each dissolved in 150 ml of demin. water and then incorporated, with stirring, into 1000 ml of an aqueous dispersion of polymer A with a solids content of 30% by weight. This corresponds to a degree of neutralization of 1.5 mol % in each case. This partially neutralized spray suspension was spray-dried analogously to example 1 in a spray tower.

The average particle size of the powder was 37 μm.

The powder was redispersed analogously to example 1 and shows a monomodal distribution with a maximum at 182 nm.

Further processing to give film tablets with an application amount of 4 mg/cm$^2$ was carried out analogously to example 1.

Testing the tablets as to resistance in buffer pH 6.8 revealed the following results:

| 30 min | 100% |
|---|---|
| 60 min | 72% |

The invention claimed is:

1. A method for producing a film-forming coating composition for a dosage form comprising at least one pharmaceutical active ingredient and a plasticizer, and having resistance to premature release of the active ingredient, the method comprising:
    providing a copolymer of N,N-diethylaminoethyl methacrylate (DEAEMA) and methyl methacrylate (MMA) having a weight ratio of DEAEMA:MMA in the range of 35:65 to 55:45, and
    partially neutralizing a powder of the copolymer or an aqueous dispersion of the copolymer to 2 to 15 mol % and a pH of 6-8 with an unsubstituted $C_3$-$C_{10}$-dicarboxylic acid to produce partially neutralized copolymers in the film-forming coating composition;
    wherein:
        the film-forming coating composition is sprayable and is obtained by applying an aqueous film-forming coating composition prepared by redispersing a powder form of the film-forming coating composition in water; and
        upon application of the coating composition in an amount of 4 mg/cm$^2$, the dosage form has a resistance to release of the pharmaceutical active ingredient in an aqueous environment at pH 6.8 of at least 80% after 30 min.

2. The method of claim 1, wherein the partially neutralizing step occurs with the dicarboxylic acid in an aqueous dispersion.

3. The method of claim 2, wherein the copolymer is partially neutralized to 4 to 10 mol %.

4. The method of claim 3, wherein the copolymer is partially neutralized with an unbranched $C_3$-$C_{10}$-dicarboxylic acid.

5. The method of claim 1, wherein the dicarboxylic acid comprises an alkane dicarboxylic acid.

6. The method of claim 5, wherein the dicarboxylic acid is selected from the group consisting of malonic acid, succinic acid, glutaric acid, adipic acid, or sebacic acid.

7. The method of claim 6, wherein the dicarboxylic acid comprises adipic acid.

8. The method of claim 1, wherein the dicarboxylic acid comprises fumaric acid.

9. The method of claim 1 further comprising redispersing the coating composition in water prior to application to a dosage form.

10. A method of making a dosage form comprising applying a film-forming coating composition produced by the method of claim 1 to an active ingredient, the film-forming coating composition providing protection against premature release of the active ingredient in an aqueous environment at pH 6.8.

11. A dosage form comprising a pharmaceutical active ingredient and a film-forming coating composition produced by the method of claim 1.

12. The dosage form of claim 11, wherein the film-forming coating composition is applied in an amount in the range of 1 to 20 mg/cm$^2$.

13. A method for producing a film-forming coating composition for a dosage form comprising at least one pharmaceutical active ingredient and a plasticizer, and having resistance to premature release of the active ingredient, the method comprising:
    dispersing a powder of a copolymer of N,N-diethylaminoethyl methacrylate (DEAEMA) and methyl methacrylate (MMA) having a weight ratio of DEAEMA: MMA in the range of 35:65 to 55:45 in a solution comprising water and a $C_3$-$C_{10}$-dicarboxylic acid thereby partially neutralizing the powder of the copolymer to 2 to 15 mol % and establishing a pH of 6-8 to produce the film-forming coating composition comprising partially neutralized copolymers;
    and
    applying the film-forming coating composition in an amount in the range of 1 to 20 mg/cm$^2$ to a core comprising the at least one pharmaceutical active ingredient to create the dosage form;
    wherein:
        the film-forming coating composition is sprayable and is obtained by applying an aqueous film-forming coating composition prepared by redispersing a powder form of the film-forming coating composition in water; and
        upon application of the coating composition in an amount of 4 mg/cm$^2$, the dosage form has a resistance to release of the pharmaceutical active ingredient in an aqueous environment at pH 6.8 of at least 80% after 30 min.

14. The method of claim 13, wherein the copolymer is partially neutralized to 4 to 10 mol %.

15. The method of claim 13, wherein a particle size of the copolymer in the film-forming coating composition is in a range of from 70 to 254 nm.

16. The method of claim 13, wherein the plasticizer selected from the group consisting of: triethyl citrate, tributyl citrate, diethyl sebacate, dibutyl sebacate, and acetyl triethyl citrate.

* * * * *